United States Patent
Szymon Suckewer et al.

(10) Patent No.: US 9,351,794 B2
(45) Date of Patent: May 31, 2016

(54) METHODS TO ALTER DAMAGED MAMMALIAN SKIN USING A MULTIPHOTON PROCESSES

(71) Applicants: Szymon Szymon Suckewer, Princeton, NJ (US); Alexander Smits, Princeton, NJ (US); Steven Hubert, Princeton, NJ (US)

(72) Inventors: Szymon Szymon Suckewer, Princeton, NJ (US); Alexander Smits, Princeton, NJ (US); Steven Hubert, Princeton, NJ (US)

(*) Notice: Subject to any disclaimer, the term of this patent is extended or adjusted under 35 U.S.C. 154(b) by 0 days.

(21) Appl. No.: 14/728,414

(22) Filed: Jun. 2, 2015

(65) Prior Publication Data
US 2015/0289935 A1   Oct. 15, 2015

Related U.S. Application Data

(63) Continuation-in-part of application No. 14/532,236, filed on Nov. 4, 2014, now Pat. No. 9,247,995, which is a continuation of application No. 13/781,287, filed on Feb. 28, 2013, now Pat. No. 8,915,907, which is a continuation-in-part of application No. 13/460,442, filed on Apr. 30, 2012, now abandoned, which is a continuation of application No. 12/136,943, filed on Jun. 11, 2008, now Pat. No. 8,187,256.

(60) Provisional application No. 60/944,388, filed on Jun. 15, 2007, provisional application No. 60/953,826, filed on Aug. 3, 2007.

(51) Int. Cl.
*A61B 18/20* (2006.01)
*A61B 18/00* (2006.01)
*A61B 17/00* (2006.01)

(52) U.S. Cl.
CPC ...... *A61B 18/203* (2013.01); *A61B 2017/00769* (2013.01); *A61B 2018/0047* (2013.01); *A61B 2018/00452* (2013.01); *A61B 2018/00458* (2013.01); *A61B 2018/00476* (2013.01); *A61B 2018/00577* (2013.01); *A61B 2018/207* (2013.01); *A61B 2018/2025* (2013.01); *A61B 2018/2095* (2013.01)

(58) Field of Classification Search
CPC ...................................................... A61N 5/062
USPC ........................................... 606/9; 607/88, 89
See application file for complete search history.

(56) References Cited

U.S. PATENT DOCUMENTS

| | | | |
|---|---|---|---|
| 8,187,256 B2 | 5/2012 | Smits et al. | |
| 2008/0154248 A1 | 6/2008 | Dunki-Jacobs | |
| 2009/0227994 A1 | 9/2009 | Grundfest et al. | |
| 2010/0082019 A1* | 4/2010 | Neev | A61B 18/203 606/9 |
| 2010/0286674 A1* | 11/2010 | Ben-Yakar | A61B 5/0059 606/10 |

* cited by examiner

*Primary Examiner* — William Thomson
*Assistant Examiner* — Jeffrey Lipitz
(74) *Attorney, Agent, or Firm* — r.r (princeton); Roy Rosser

(57) ABSTRACT

A system and method of altering damaged mammalian skin using a multiphoton processes is disclosed. A femtosecond laser initiates a multiphoton event using pulse energies of 2-5 mJ thereby causing multiphoton ablation without damaging surrounding tissue. The laser is focused to the vicinity of a target organelle that occurs naturally within the damaged skin, and is related to the dermatological condition being addressed. The type of organelle depends on the condition being addressed, and may be targeted by the depth beneath the surface of the skin at which it is located. The femtosecond laser beam is focused to an intensity of least $10^{12}$ W/cm$^2$ to initiate the multiphoton event transforms the targeted organelle to mitigate the damage to the skin.

5 Claims, 4 Drawing Sheets

METHODS TO ALTER DAMAGED MAMMALIAN SKIN USING A MULTIPHOTON PROCESSES

CROSS-REFERENCE TO RELATED APPLICATIONS

This application is a continuation-in-part of U.S. patent application Ser. No. 14/532,236 filed on Nov. 4, 2014, which in turn is a continuation of U.S. patent application Ser. No. 13/781,287 filed on Feb. 28, 2013 that issued as U.S. Pat. No. 8,915,907 on Dec. 23, 2014 which in turn is a continuation-in-part of U.S. patent application Ser. No. 13/460,442 filed on Apr. 30, 2012 that is a continuation of U.S. patent application Ser. No. 12/136,943 filed on Jun. 11, 2008 that issued as U.S. Pat. No. 8,187,256 on May 29, 2012, the contents of all of which are hereby incorporated by reference.

This application is further related to, and claims priority from, U.S. Provisional Patent application No. 60/944,388 filed on Jun. 15, 2007 and to U.S. Provisional Patent application No. 60/953,826 filed on Aug. 15, 2007 the entire contents of both of which are hereby incorporated by reference.

FIELD OF THE INVENTION

The invention relates to a method and apparatus for altering damaged mammalian skin, and more particularly to using a multiphoton process initiated using ultrashort laser pulses to make the alterations.

BACKGROUND OF THE INVENTION

A variety of laser treatments have Federal Drug Administration (FDA) approval for a wide range of dermatological conditions ranging from scar tissue removal, reduction of birthmarks and other pigment related problems including lentiginous conditions such as freckles, liver spots and sun damaged skin, to wrinkle reduction and skin tightening. Although each approved treatment may use a different laser, each of which may have a different wavelength and power, there are some commonalities among the array of lasers currently used in these dermatological treatments.

The most important may be that they all have pulse-widths in the nanosecond range. Although the individual pulse powers are relatively low—typically about 200 mJ per pulse—the long pulse-widths allow time for the heat produced to diffuse out. This diffusion not only means that more total energy has to be delivered in the form of a greater number of pulses—lengthening the time for a typical procedure to 1 to 2 hours—but also that the surrounding tissue may be heated significantly—typically to the extent of a second-degree burn. This has, in the past, made laser procedures painful at the time, and required recovery times of 1 to 2 weeks. The industry has attempted to address the pain factor by developing a range of topical anesthetics to be applied during the procedures. They have also developed ways of cooling the surrounding tissue using a variety of methods from cool air jets, water spray to having piezoelectric cooling heads as part of the laser delivery head.

These advances have mitigated the pain and recovery problems significantly, though not completely. The cooling systems may be difficult to apply, and the powerful topical anesthetics pose risks in of themselves.

What is needed is a system that can deliver the benefits of laser dermatological procedures without the side-effects, particularly the heating or damage to the surrounding tissue, and in much reduced treatment times.

BRIEF SUMMARY OF THE INVENTION

An inventive system and method of altering damaged mammalian skin using a multiphoton processes is disclosed.

The current invention preferably utilizes a femtosecond laser whose pulse lengths are sufficiently short that the required intensity to initiate a multiphoton event may be reached with pulse energies as low as 2-5 mJ.

The interaction of the ultrashort, femtosecond laser pulses with biological tissue may be fundamentally different than that which occurs in a single photon interaction with such tissue.

In a multiphoton process, the ultrahigh intensity laser pulses create electrical fields in a vicinity of the tissue particles that may be comparable, or even greater, than the Coulomb field in the molecules, atoms and ions that constitute the tissue particles. The multiphoton process may, for instance "take apart" the particles, i.e., it may separate molecules into their component atoms, effectively freeing them from the tissue in a process termed "multiphoton ablation". This process may occur with practically no heating of the tissue. This makes the "multiphoton ablation" of tissue fundamentally different than the ablation of tissue achieved using nanosecond-type lasers.

With nanosecond-type lasers, ablation is achieved a single photon at a time and is a thermal process. Each photon absorbed in "single photon" ablation results in electron heating that may be distributed to many nearby particles. Typical nanosecond-type laser pulses have intensities that may be many orders of magnitude lower than that used to achieve a multiphoton process. Enough electron heating, therefore, has to be accumulated over a significant number of individual photon absorption events in order for ablation to occur. Single photon, nanosecond time scale ablation, therefore, takes a long enough time that a significant faction of the energy being applied to achieve ablation may diffuse away from the focal region in the form of waste heat, and may cause significant heat damage to the surrounding tissue.

In contrast, "multiphoton ablation", is made possible through the use of ultrashort laser pulses that produce local energy intensities that may be many orders of magnitude higher than those produced by nanosecond laser pulses. These high intensities may allow many photons to be absorbed simultaneously, resulting in ablation occurring on a time scale shorter than the radiative relaxation time of any of the atoms or molecules of the tissue. Individual atoms and molecules may, therefore, absorb a total energy larger than their atomic binding energy from a single femtosecond laser pulse. The particles are, therefore, "taken apart", or ablated, without any significant loss, or waste, of energy in the form of heat that may diffuse to, and damage, the surrounding tissue.

A laser may be focused in the vicinity target, typically a specific type of organelle that occurs naturally within the damaged skin, and which may be related to the dermatological condition being addressed. The type of organelle may depend on the dermatological condition being addressed, and may be targeted by, for instance, the depth beneath the surface of the damaged skin at which the organelle is known to be located.

The focal region of the femtosecond laser beam preferably may have an intensity in a range of equal or more than $10^{12}$ W/cm$^2$ which may be sufficient to initiate a multiphoton event. This multiphoton event or process may then alter or transform one or more instantiations of the targeted organelle in such a way as to mitigate the damage of the damaged skin.

It is an object of the invention to provide improved techniques of addressing dermatological conditions with a minimum of burning of the skin, scarring of the skin, and pain through the use of a laser multiphoton processing.

It is another object of the invention to provide improved techniques of addressing dermatological conditions which can be performed more quickly than prior methods.

DETAILED DESCRIPTION OF THE INVENTION

Figure 1:
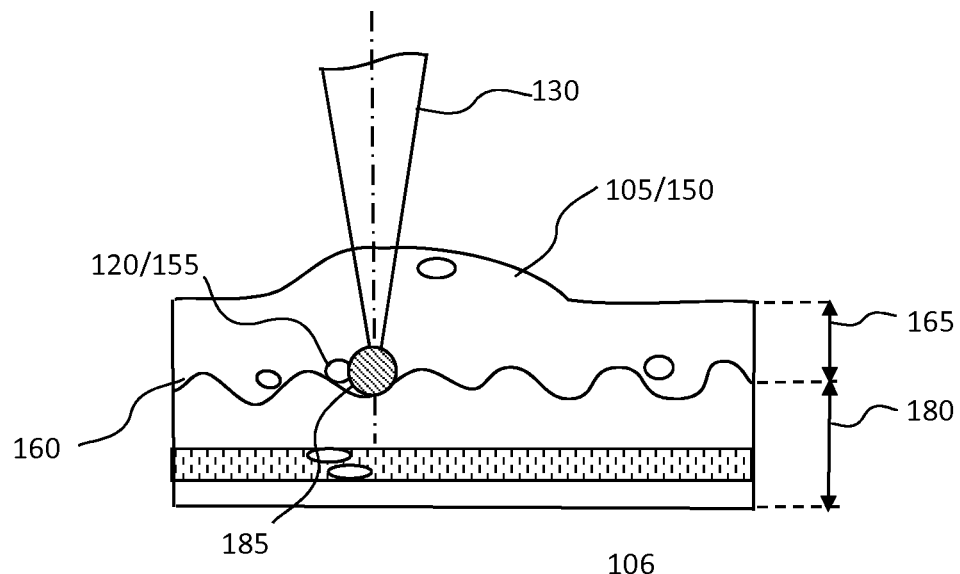
FIG. 1 shows a schematic of altering damaged mammalian skin using multiphoton processing to destroy a melanocyte.

The preferred embodiments of the present invention will now be described with reference to the drawings. Identical elements in the various figures are identified with the same reference numerals.

Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

The Femtosecond Laser

The laser beam may be tightly focused to a small sized focal region, or spot, so as to achieve an ultrahigh intensity in a vicinity of the organelle to be altered, and, thereby, alter the organelle. Preferably, the laser will be a femtosecond laser with: a relatively low energy, for example in the range of 2 to 5 mJ/pulse; a pulse duration in the range of 50 to 100 fsec, although a range of 10 to 1000 fsec is possible; a focal spot diameter in the range of 20 to 100 micrometers, although the diameter could be smaller or greater depending on the focal spot diameter of the first laser; and a preferred intensity in the range of $10^{13}$ to $10^{15}$ W/cm$^2$, although a range of $10^{12}$ to $10^{16}$ W/cm$^2$ may be used. The laser beam's wavelength is preferably 800 nm as this has been found to be an effective wavelength, although it may have a different wavelength, though this may reduce the efficacy of the beam. Repetition rates of 5 to 100 Hz may be used as these have been found to be effective rates for operating the femtosecond lasers when used for dermatological applications such as those described with regard to the current invention, although repetition rates of 1 kHz and higher may also be used. These higher repetition rates may, however, result in reduced efficiency. By way of example, one or more variants of the well-known Ti/Sapphire laser system may play the role of the femtosecond laser.

In a preferred embodiment, the femtosecond laser's ultrashort and ultraintensive beam may initiate multiphoton processes, also called here multiphoton ablation that may alter the targeted organelles and associated molecular bonding without providing any significant heat or local skin burning. Photoablated organelles may, for instance, be removed by migrating down to blood vessels in the dermis that may then transport them away from the region. Dermatological conditions may be addressed multiple times in significantly shorter intervals compared to thermal laser-based dermatological treatments where burns caused by the laser treatment must be given time to heal between treatments.

In contrast to a thermal ablation process, which is typically generated by relatively low intensity but relatively high energy laser pulses that may initiate a single-type photon absorption process, multiphoton processing or ablation, utilizes a very high intensity laser pulse, i.e., many photons in a small volume at the same time, where the density of photons is so great that during an absorption event many photons are absorbed almost simultaneously, which means that these many photons are absorbed by a particle, such as a molecule, atom, or ion, in a time period that is shorter than the relaxation time of the given particle.

Multiphoton processing also differs from thermal photoablation in that the low amount of energy per pulse involved in multiphoton processing allows the ablation to be very localized, very fast and result in no or negligible thermal heating or shocking of any surrounding material. For instance, by focusing a 2 mJ pulse of laser light that has a temporal pulse length in the range from 100 to 300 femtoseconds in duration—although the pulse duration could be shorter, for example 10 fsec, or longer, for example 500 fsec and even longer—to a small enough focal spot so the intensity is equal to or greater than $10^{12}$ Watts/cm$^2$, a multiphoton processing event may be initiated. This may result in the alteration of the targeted organelles. Such pulses may be obtained from, for instance, a suitably configured Titanium doped Sapphire (Ti: Sapphire) solid state laser.

The number of photons absorbed simultaneously by the particles in multiphoton ablation may be in the range of 5 to 10 photons per particle on the low end, and 100 photons or more per particle on the high end. The density of photons in a pulse is so high that the number of photons absorbed simultaneously is very large; hence multiphoton ablation may occur even where the energy of the pulse is low, in the range of 2 to 5 mJ or less. This amount of energy is sufficiently low that little or no damaging thermal heating of the surrounding tissue occurs. This is in marked contrast to thermal ablation produced with low intensity pulsed lasers where only a single photon is absorbed in any given absorption event. In such a process, the energy needed to achieve the condition for ablation may be significant. Typically, the energy required for thermal ablation—and which is accumulated by the tissue at the focal region—is such that the surrounding tissue typically incurs significant heat damage as that accumulated energy diffuses way from the focal region.

The processes that involve several photons in a tissue absorption event in thermal ablation processes are sometimes inaccurately referred to in the literature as "multiphoton processes".

For a multiphoton process to be useful for addressing most dermatological issues, the intensities of the laser pulses have to be very high. One way to simultaneously achieve both the high intensity and low energy is by using ultrashort laser pulses and focusing them down to a small sized spot or focal region. In laser physics, ultrashort pulses are typically defined to be pulses up to 10 psec in duration, but preferably 50 to 100 fsec or even shorter. Moreover, the multiphoton ablation process is practically independent of the specific type of organelle targeted. Using multiphoton processing address dermatological issues does not, therefore, require using different laser wavelengths for different conditions. This is in sharp contrast to thermal photoablation processes where the wavelength has to be chosen carefully to maximize the interaction with the different organelles associated with different dermatological conditions.

When the laser wavelength used in the present invention are in the infrared, they may penetrate deep into the dermis. The necessary high intensities in the vicinity of the target material may therefore be accomplished within the focal volume and made to exceed the threshold intensity necessary to initiate multiphoton processing by appropriate adjustment of the focal spot.

Dermatological Conditions Addressed.

Currently, there are lasers that have FDA approval to treat a variety of vascular lesions including superficial vascular malformations (port-wine stains), facial telangiectases, rosacea related erythema/redness, hemangiomas, pyogenic granulomas, Kaposi sarcoma and poikiloderma of Civatte.

Pigmented lesions that are treated include lentiginous regions and birthmarks including some congenital melanocytic naevi, blue naevi, naevi of Ota/Ito, and Becker naevi. These systems treat the lesions by confining their energy to the melanosomes, which are the tiny granules containing melanin inside the pigment cells and other skin cells.

Lasers are also be used to remove excessive and cosmetically undesired hair due to hypertrichosis or hirsutism.

Lasers may also be used to disable or reduce the effectiveness of an eccrine gland in order to decrease perspiration in an individual with excess sweating or hyperhidrosis. A very high intensity and very well localized laser beam interacting with tissue can be very effective for treatment the excess sweating or hyperhidrosis.

Facial wrinkles, acne scars and sun-damaged skin have also been treated with lasers, but the side effects of treatment typically include post-operative tenderness, redness, swelling and scarring. The redness and tenderness may last several weeks, while new skin grows over the area where the damaged skin has been removed by the laser treatments. Bacterial, fungal and viral skin infections, including reactivation of herpes virus, are also potential complications of current laser therapy until healing occurs. Extreme caution is needed when treating darker skinned individuals as permanent loss or variable pigmentation may occur long term. Keloids and hypertrophic scars are difficult to eradicate and traditional treatments are not always successful.

The multiphoton approach of the current invention may address any or all these issues. However, it may be able to do this with a significant reduction in the pain, swelling, or scarring incurred by the process.

Moreover, the conditions may be addressed in a very short time span. For example, it has been shown that the removal of lentigenes may be addressed in a single session.

The multiphoton process appears to avoid any significant damage to the naturally occurring melanin in the skin.

The multiphoton process may, in practice, be independent of the wavelength of the laser light. This is in marked contrast to current methods that typically require matching a specific laser to a specific treatment. In the system and method of the present invention, a single laser type may be used to address a wide variety of dermatological conditions.

FIG. 1 shows a schematic of altering damaged mammalian skin 106 using multiphoton processing to destroy a melanocyte.

The laser beam 130 may be focused to a focal region 185 in a vicinity of a specific type of organelle 120 that naturally occurs within the damaged skin. Within this focal region 185, the intensity may equal or exceed $10^{12}$ W/cm² which may be sufficient to initiate a multiphoton process in the vicinity of the naturally occurring type of organelle and transforming one or more instantiations of the organelle in such a way as to mitigate the damage of the damaged skin.

FIG. 1 shows a schematic diagram of the method this invention being used to address a portion of damaged mammalian skin 105 that may be classified as a lentigo 150 or having lentigines. This is a pigmented lesion commonly called "liver-sports". Other examples of lentiginous regions include, but are not limited to, birthmarks, freckles and a variety of melanoma or melanoma related conditions. These may be caused by a hyperplasia of melanocytes—i.e. a proliferation in the number of melanocytes, the cells that produce the melanoma that provides pigmentation to the skin. These cells reside in the basal region 160, or base, of the epidermal layer 165 of the skin, and the hyperplasia of melanocytes typically only spreads horizontally along this layer. These cell may, therefore, be targeted by focusing the laser beam 130 in a vicinity of the basal layer 160 within the portion of damaged mammalian skin 105, in this instance the lentigo. The resultant multiphoton process may then destroy one or more instantiations of the melanocytes 155 in such a way as to mitigate the appearance of the damaged skin.

Figure 2:
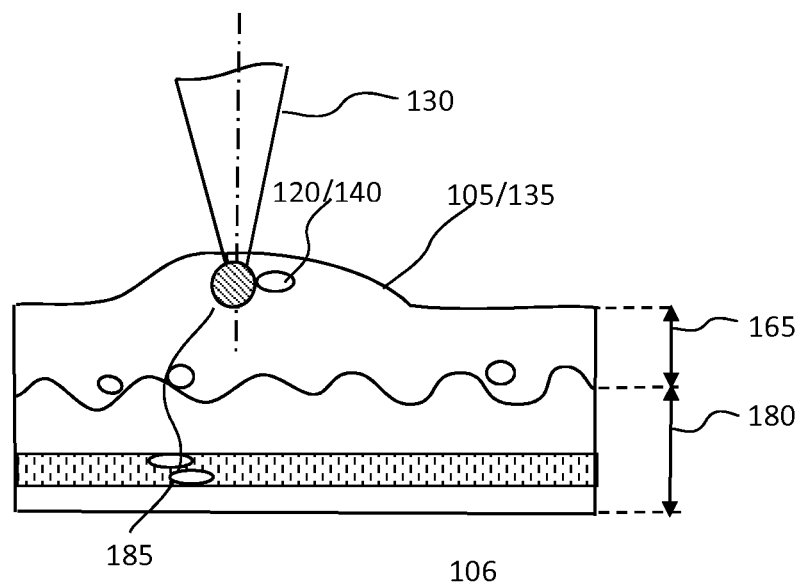
FIG. 2 shows a schematic of altering damaged mammalian skin using multiphoton processing to destroy a collagen fiber.

FIG. 2 shows a schematic of altering damaged mammalian skin using multiphoton processing to destroy a collagen fiber.

In this instance the portion of damaged mammalian skin 105 may be a region of scar tissue 135 that may be a result of a buildup of collagen fiber 140, another specific type of organelle 120 that occurs naturally within the damaged skin.

By focusing the laser beam 130 near the surface of the damaged skin, the focal region 185 may reside in a vicinity of one or more collagen fibers 140. The resultant multiphoton process may then destroy one or more instantiations of collagen fibers 140 in such a way as to reduce the scar tissue that may be the damage to the skin.

Figure 3:
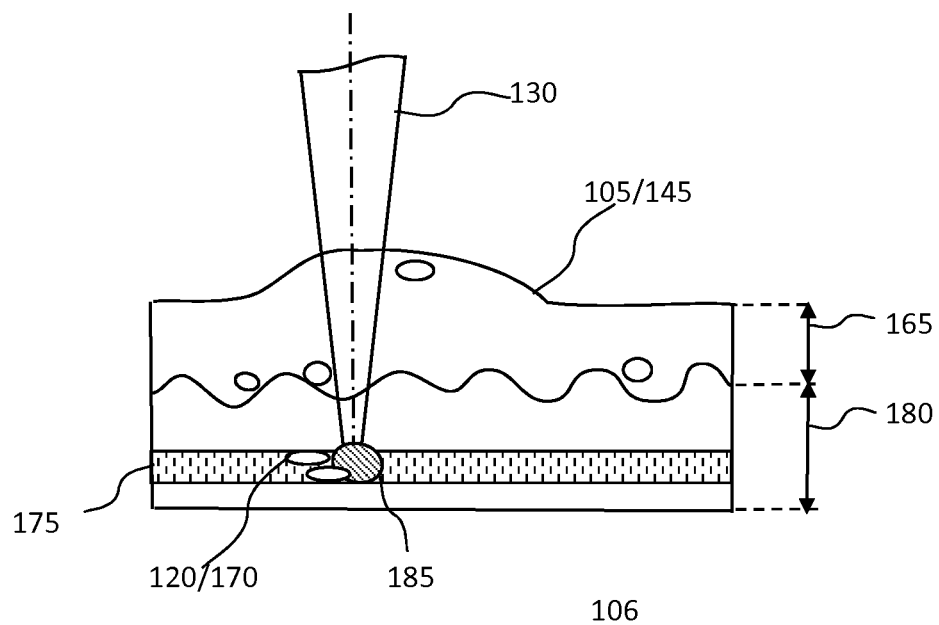
FIG. 3 shows a schematic of altering damaged mammalian skin using multiphoton processing to cross-link two or more adjacent collagen fibers.

FIG. 3 shows a schematic of altering damaged mammalian skin using multiphoton processing to cross-link two or more adjacent collagen fibers.

In this instance, the portion of damaged mammalian skin 105 may be a surface wrinkle 145. These may be caused by collagen fibers 170 within the connective tissue 175 within the dermal layer 180, the layer immediately below the epidermal layer 165 of the skin.

By focusing the laser beam 130 to a focal region 185 within the connective tissue 175, a multiphoton process may be initiated, but by adjusting the power level of the laser, the multiphoton process may not obliterate the natural organelles 120, but instead cause two or more adjacent collagen fibers 170 to cross-link. The additional cross-linking may strengthen the connective tissue 175, tightening the skin and mitigating the surface wrinkle 145.

Figure 4:
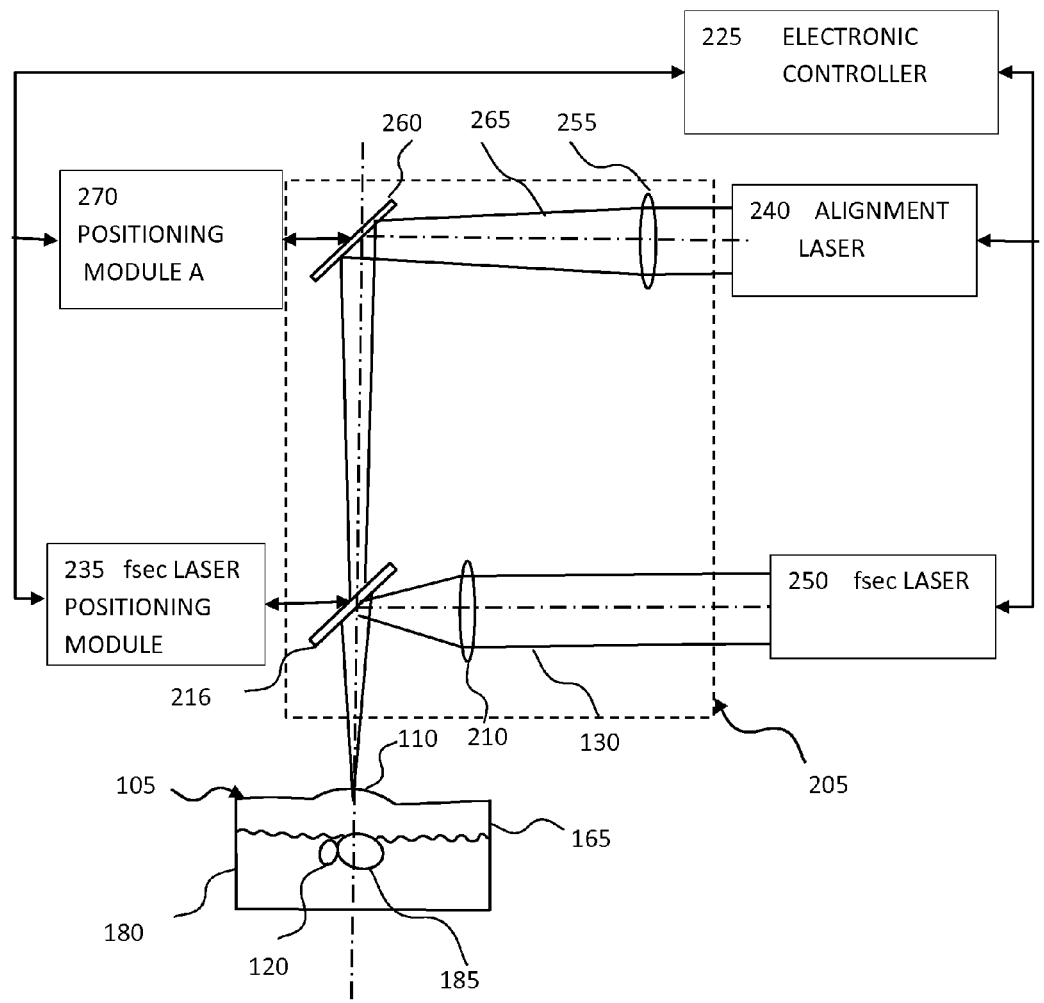
FIG. 4 shows a schematic drawing of an exemplary embodiment of an apparatus for performing the present invention.

FIG. 4 shows a schematic drawing of an exemplary embodiment of an apparatus for performing the present invention.

A femtosecond laser 250 may be focused into or onto a portion of damaged mammalian skin 105, beneath the surface 110 of the damaged skin, by means of an optical system 205. The femtosecond laser 250 may, for instance, possess the attributes described above in the section "Femtosecond Laser".

The focal region 185 of the laser may be adjusted to be within the vicinity of a specific type of organelle 120 that naturally occurs within the damaged skin, and which may contribute to the damage. This focusing of the femtosecond laser beam 130 may, for instance, be accomplished using a first laser beam focusing element 210. The first laser beam focusing element 210 and/or a laser beam combiner 216 may be controlled by a femtosecond laser beam positioning module 235. This module may in turn be controlled by an electronic controller 225, either automated, or semi-automated under the control of an operator. The electronic controller 225 may also control the femtosecond laser.

In a preferred embodiment, the system may further include a low power alignment laser 240, such as, but not limited to, to a Helium-Neon laser.

The alignment beam 265 may be focused by an alignment beam focusing element 255 and positioned by an alignment beam positioning module 270 and an alignment beam combiner 260. The focus of the alignment laser 240 may be made coincident with the focal region 185 of the femtosecond laser 250, and may serve to guide an operator in setting up the apparatus.

Both the alignment beam positioning module 270 and the alignment laser 240 may also be controlled by the electronic controller 225 that may, for instance, be a suitably programmed digital processor and associated digital memory.

Figure 5:
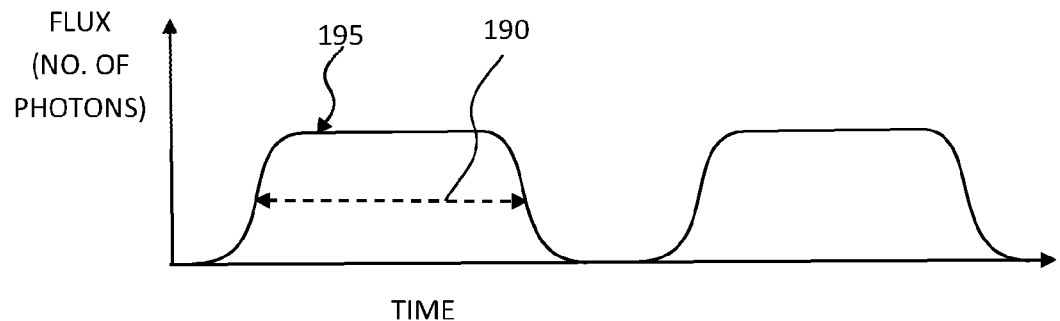
FIG. 5 shows a schematic representation of a train of laser pulses.

FIG. 5 shows a schematic representation of a train of laser pulses. The illustration of FIG. 5 is intended to show how the flux, or number of photons, varies with time in a pulsed laser system. In particular the pulse length 190 of the pulse 195 is clearly illustrated.

In a further preferred embodiment of the invention, a two-beam laser system as described in detail in, for instance, U.S. Pat. No. 8,915,907 issued on Dec. 23, 2014 and which is hereby incorporated by reference, may be adapted for use in demagogical applications. Applications such as, but not limited to, hair removal that requires a focal region beneath the dermis, may benefit from the use of a second laser that creates a waveguide to the target for the femtosecond laser, helping minimize absorption losses.

The femtosecond pulses 305 may be transmitted to the area of interest on the patient via a delivery optic, a fiber optic 325 and a delivery wand 330. The delivery optic may, for instance, be a flat or focusing mirror used to direct the femtosecond pulses 305 into the fiber optic 325. The fiber optic 325 may, for instance, be any glass or plastic fiber having the requisite transparency to the femtosecond pulses 305. The fiber optic 325 may be used to transport the femtosecond pulses 305 to the delivery positioning unit that may be under the control of a control computer.

The delivery wand 330 may also deliver a guidance light beam 345. The mixing optic may assist in delivering the guidance light beam 345 to the fiber optic 325 or the delivery wand 330. The mixing optic may, for instance, be a suitable multilayer mirror that reflects the guidance light beam 345 but is transparent to the femtosecond pulses 305. The guidance light beam 345 may, for instance, be from a Helium Neon laser, although any other laser with an output in the visible spectrum would be suitable. The guidance light source 355 may include a detector for monitoring how much of the guidance light beam 345 is reflected back from the surface of the patient 375. In this way a feed-back loop may be established to monitor the distance between a focusing tip of the delivery wand 330 and the patient.

Figure 6:
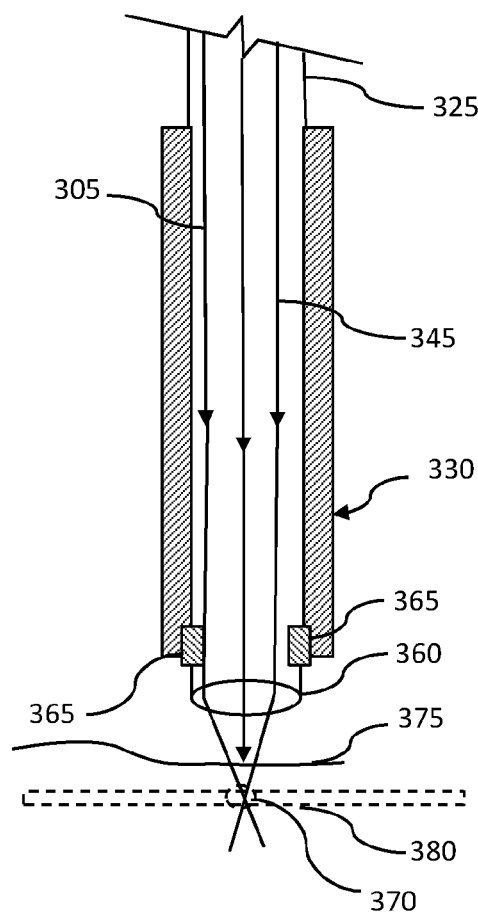
FIG. 6 is a cross-sectional drawing of an exemplary delivery wand of the present invention for providing multi-photon processing treatment.

FIG. 6 is a cross-sectional drawing of an exemplary delivery wand 330 of the present invention for providing multi-photon processing treatment. The delivery wand 330 may include a short focal length lens 360, one or more micro-positioning elements 365 and a fiber optic 325. The fiber optic 325 may deliver the femtosecond pulses 305 and the guidance light beam 345 to the short focal length lens 360. The short focal length lens 360 focuses the femtosecond pulses 305 to a focal volume 370 that is positioned beneath a surface of the patent 375 in the vicinity of the pigmented layer 380. The pigmented layer 380 is typically located about 1 to 2 mm beneath the surface of the patent 375.

The focal volume 370 may be 500 µm in diameter or smaller. In a preferred embodiment, the focal volume 370 may be made substantially equal to the thickness of the pigmented layer 380 that may be as small as 5 µm.

The power density in the focal volume 370 typically needs to be in the range of $10^{12}$-$10^{13}$ Watts/cm$^2$ in order to initiate a multi-photon processing event. With very long wavelength lasers such as, but not limited to, the 10 µm wavelength CO2 laser, multi-photon processing events may be initiated when the power density in the focal volume 370 is in the range of $10^{11}$ Watts/cm$^2$.

The delivery wand 330 may also deliver a guidance light beam 345 that may be a Helium Neon laser beam or some other suitable visible light laser. A portion of the guidance light beam 345 may be reflected off the surface of the patent 375 and back up the delivery wand 330. This reflected portion of the guidance light beam 345 may be detected by, for instance, a suitably located photo-diode. The reflected portion of the guidance light beam 345 may then be used as a feedback loop and used to control the location of the focal volume 370 relative to the surface of the patent 375 using the micro-positioning elements 365. The micro-positioning elements 365 may, for instance, be piezoelectric devices, or they may be MEMS actuated devices or they may be micro-mechanical devices controlled by, for instance, electric motors.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed:

1. A method of altering a portion of mammalian skin to mitigate the appearance of a lentigo, comprising:
   providing a portion of mammalian skin having said lentigo, said lentigo comprising a lentiginous region having a hyperplasia of melanocyte cells located at a basal region of an epidermal layer of said mammalian skin;
   locating a surface of said mammalian skin by focusing a visible light laser onto said mammalian skin via a lens and monitoring a reflected portion of said focused light; and
   focusing a femtosecond laser relative to said located surface of said skin by adjusting a position of said lens using a micro-positioning element, thereby focusing said femtosecond laser to a focal point located coincident with said basal region of said epidermal layer of said skin within said lentiginous region, said femtosecond laser having a wavelength in a range of 0.2 µm to 10 µm, a pulse length less than 300 femtoseconds, a pulse energy less than or equal to 2 mJ and a focal volume of 50 µm or less, thereby creating an intensity within said focal region of at least $10^{12}$ W/cm$^2$, thereby initiating a multiphoton process that destroys one or more melanocyte cells and mitigates said lentigo.

2. The method of claim 1, wherein said laser beam has a pulse length of 100 fsec or less.

3. The method of claim 2, further comprising an optical system having a laser beam focusing element.

4. The method of claim 3, wherein adjusting said optical system further comprises an electronic controller and a laser beam positioning module.

5. The method of claim 1, wherein the laser beam is pulsed at a repetition rate in a range of 5 to 100 Hz.

\* \* \* \* \*